US006660785B2

(12) United States Patent
Klee et al.

(10) Patent No.: US 6,660,785 B2
(45) Date of Patent: Dec. 9, 2003

(54) SELF-ADHESIVE POLYMERIZABLE MONOMER AND DENTAL/MEDICAL COMPOSITIONS THEREFROM

(75) Inventors: Joachim E. Klee, Radolfzell (DE); Uwe Walz, Constance (DE)

(73) Assignee: Dentsply DeTrey GmbH (DE)

( * ) Notice: Subject to any disclaimer, the term of this patent is extended or adjusted under 35 U.S.C. 154(b) by 124 days.

(21) Appl. No.: 10/044,345

(22) Filed: Jan. 11, 2002

(65) Prior Publication Data

US 2002/0082318 A1 Jun. 27, 2002

Related U.S. Application Data

(63) Continuation of application No. 09/541,831, filed on Apr. 3, 2000, now abandoned.
(60) Provisional application No. 60/133,824, filed on May 12, 1999.

(51) Int. Cl.$^7$ ............................................. A61K 6/083
(52) U.S. Cl. .................... 523/116; 423/228.1; 523/117; 523/118; 526/239; 526/278; 526/287; 526/312
(58) Field of Search ................ 433/228.1; 523/116, 523/117, 118; 526/239, 278, 287, 312

(56) References Cited

U.S. PATENT DOCUMENTS

| | | | |
|---|---|---|---|
| 399,754 A | 3/1889 | Keep | 73/792 |
| 2,709,690 A | 5/1955 | Narracott | 528/111.5 |
| 4,383,052 A | 5/1983 | Higo et al. | 523/118 |
| 4,514,342 A | 4/1985 | Billington et al. | 433/228.1 |
| 4,612,384 A | 9/1986 | Omura et al. | 558/198 |
| 4,657,941 A | 4/1987 | Blackwell et al. | 522/14 |
| 4,674,980 A | 6/1987 | Ibsen et al. | 433/228.1 |
| 4,806,381 A | 2/1989 | Engelbrecht et al. | 427/2 |
| 5,321,053 A | 6/1994 | Hino et al. | 522/26 |
| 5,705,581 A | 1/1998 | Fife et al. | 523/248 |
| 5,710,194 A | 1/1998 | Hammesfahr et al. | 523/116 |
| 5,730,601 A | 3/1998 | Bowman et al. | 433/228.1 |

FOREIGN PATENT DOCUMENTS

| | | |
|---|---|---|
| DE | 3150285 | 7/1982 |
| EP | 074708 | 3/1983 |
| EP | 088527 | 9/1983 |
| EP | 115410 | 8/1984 |
| EP | 058483 | 10/1986 |
| EP | 328772 | 8/1989 |
| EP | 554890 | 8/1993 |
| EP | 897709 | 2/1999 |
| WO | 98/46196 | 10/1998 |

*Primary Examiner*—Peter Szekely
(74) *Attorney, Agent, or Firm*—Douglas J. Hura; James B. Bieber

(57) ABSTRACT

The synthesis of self-adhesive polymerizabe monomers and their application as a water containing and a water free self-adhesive dental/medical composite is described. The dental/medical composite comprises a self-adhesive polymerizabe monomer, a polymerizable monomer, an acid-reactive and/or reactive and/or non-reactive filler, a diluent, a polymerization initiator and a stabilizer. As polymerization initiators are used the commonly known thermal initiators, redox initiators and/or photo initiators. The new adhesive dental composite develops adhesion to dentine of about 4 MPa. Fillers of high X-ray absorbance provide radio-opacity values grater than that of the same thickness of aluminium.

2 Claims, No Drawings

SELF-ADHESIVE POLYMERIZABLE MONOMER AND DENTAL/MEDICAL COMPOSITIONS THEREFROM

RELATED APPLICATION

This application is a continuation of Ser. No. 09/541,831 filed Apr. 3, 2000, now abandoned, which claims the benefit of U.S. Provisional Application Serial No. 60/133,824 filed on May 12, 1999.

TECHNICAL FIELD

The invention relates to self-adhesive polymerizable monomers suitable for dental and medical applications.

BACKGROUND OF THE INVENTION

Conventional dental/medical compositions such as cements are either water-based ionic cements or resin based materials. The water-based cements have the advantage of a modest adhesion to hard tooth tissues and of a high fluoride ion release from inorganic filler material. They have the disadvantage of high water solubility, low abrasion resistance and an excessive opacity. The resin-based materials have the advantage of excellent mechanical properties, a suitable opacity and low water solubility. They have the disadvantage of a lack of adhesion, a very poor release of fluoride ions from an inorganic filler and a high shrinkage.

It has already been known to improve the adhesion of resin-based dental/medical composites by incorporation of phosphoric acid ester groups or carboxylic ester groups (U.S. Pat. Nos. 399,754, 2,709,690, 4,514,342, 4,806,381, DE-OS 3536077, DE-OS 2711234, EP 0058483, DE-OS 3150285, E. Masuhara et.al. Rep. Inst. Med. Dent.Eng. 1 (1967) 29–33, M. Takeyama et. al. J.Soc.Dent.Appar. 19 (1978) 179–185). However, the adhesion is still insufficient. Moreover compositions with such monomers have a high shrinkage during polymerization.

It is a problem of the invention to provide a self-adhesive polymerizabe monomer for dental compositions and a process for preparing said self-adhesive polymerizabe monomer, whereby the dental/medical composition which combine the favourable characteristics of water-based and resin-based conventional materials and have a high adhesion to hard dental tissue and lower shrinkage.

DESCRIPTION OF THE INVENTION

A self-adhesive polymerizable monomer that comprises at least two polymerizable moieties (i), at least one substituted or unsubstituted $C_3$ to $C_{20}$ alkylene or at least one substituted or unsubstituted $C_5$ to $C_{20}$ cycloalkylene (ii) that is connected with (i) by a linking unit, at least an acidic moiety selected from the group (iii)

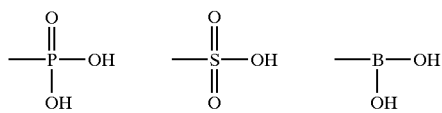

or at least an ionic moiety selected from the group

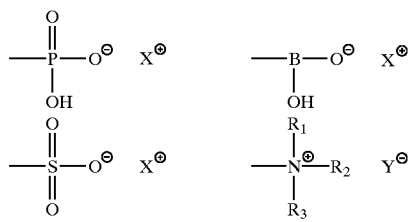

which is connected with (ii) and wherein the $R_1$, $R_2$, $R_3$ are the same or different substituted or unsubstituted residues of hydrogen or an alkylene having 2 to 20 carbon atoms, a cycloalkylene having 5 to 20 carbon atoms, an aryl or a heteroaryl having 4 to 12 carbon atoms, X is a cationic counterion such as

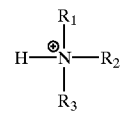

and

Y is an anionic ion such as $OH^-$, $F^-$, $Cl^-$, $Br^-$, $Tosyl^-$.

The polymerizable groups preferably are methacrylic or acrylic groups. The linking unit preferably is an ether or a thioether, an ester, a carbonate, a urethane moiety.

Preferably, the self-adhesive polymerizable monomer is characterized by the following formulas:

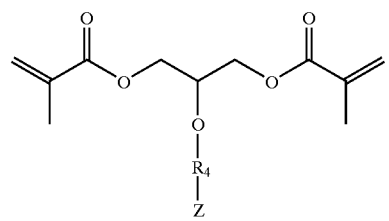

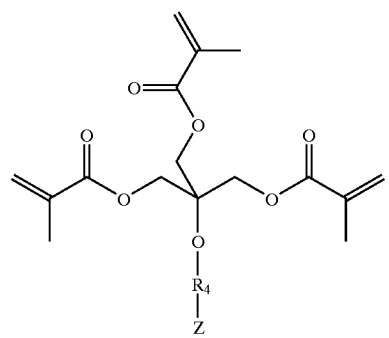

wherein
R₄ denotes a substituted or unsubstituted alkylene having 3 to 20 carbon atoms,
Z is an acidic moiety selected from the group

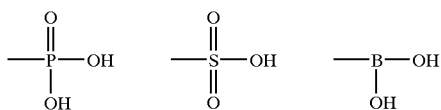

or an ionic moiety selected from the group

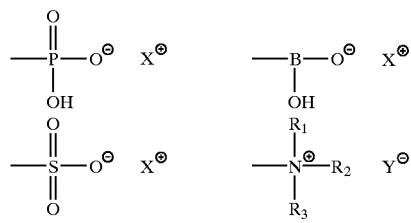

wherein
the $R_1$, $R_2$, $R_3$ are the same or different substituted or unsubstituted residues of Hydrogen or an alkylene having 2 to 20 carbon atoms, a cycloalkylene having 5 to 20 carbon atoms, an aryl or a heteroaryl having 4 to 12 carbon atoms,
X is a cation such as ammonium, sulfonium, sodium, potassium, strontium, calcium or magnesium salts

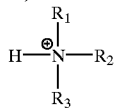

and
Y is an anion such as OH—, F—, Cl—, Br—, Tosyl—.
Most preferably the self-adhesive polymerizable monomer is characterized in the following formula:

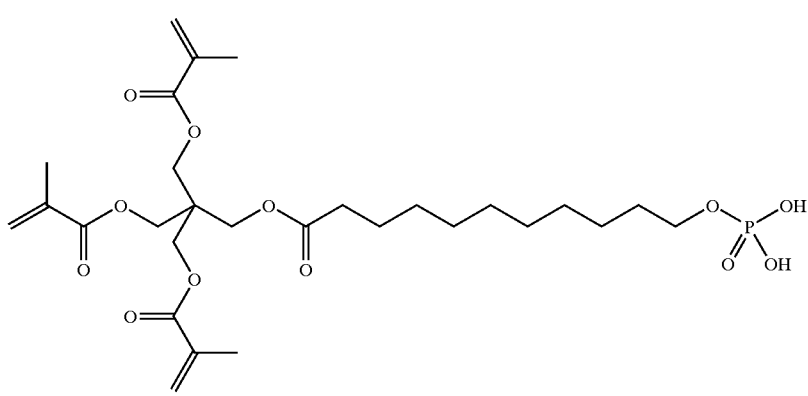

The self-adhesive polymerizable monomer is used in a dental/medical composition comprising a filler, a polymerizable monomer, a polymerization initiator and a stabilizer.

The polymerizable monomer preferably is a mono- and polyfunctional (meth)acrylate, such as a reaction product of a polyepoxide with (meth)acrylic acid), a polyalkylenoxide di- and poly(meth)acrylate, an urethane di- and poly(meth)acrylate, preferably were used Bis-GMA diethylenglycol dimethacrylate, triethylenglycol dimethacrylate, 3,(4),8,(9)-dimethacryloyloxymethyltricyclodecane, dioxolan bismethacrylate, glycerol trimethacrylate, furfuryl methacrylate in a content of 5 to 80 wt-%.

The polymerization initiator is a thermal initiator, a redox-initiator or a photo initiator.

As filler is an inorganic filler and/or an organic filler.

The self-adhesive polymerizable monomer is usable in a self-adhesive dental/medical composition characterized by the combination of A an adhesion to dentine of at least 5 MPa B a fluoride release of at least 1 μg F⁻ per week and per cm² of the exposed surface of the composition C an opacity of at least $C_{0,7}$=40% and D a compressive strength of at least 200 MPa.

The self-adhesive polymerizable monomer is usable in a self-adhesive dental/medical cement comprising 25 to 50 wt-% of a self-adhesive polymerizable monomer, 0 to 25 wt-% of a polymerizable monomer, 50 to 75 wt-% of a filler and polymerization initiator and stabilizers.

The self-adhesive polymerizable monomer is usable in a self-adhesive dental/medical composite comprising 15 to 50 wt-% of a self-adhesive polymerizable monomer of claims 1 to 3, 0 to 35 wt-% of a polymerizable monomer, 50 to 85 wt-% of a filler and polymerization initiator and stabilizers.

The self-adhesive polymerizable monomer is usable in a self-adhesive dental/medical sealant comprising 45 to 90 wt-% of a self-adhesive polymerizable monomer of claims 1 to 3, 0 to 45 wt-% of a polymerizable monomer, 10 to 55 wt-% of a filler and polymerization initiator and stabilizers.

The self-adhesive polymerizable monomer is usable in a self-adhesive dental/medical primer comprising 15 to 80 wt-% of a self-adhesive polymerizable monomer of claims 1 to 3, 0 to 65 wt-% of a polymerizable monomer, 0 to 65 wt-% of a filler and polymerization initiator and stabilizers 20 to 85 wt-% of a diluent and polymerization initiator and stabilizers.

An adhesive dental composite containing radiopaque fillers provides a radio-opacity of at least 2 mm/mm Al, preferably at least 3 to 7 mm/mm Al, most preferably at least 7 mm/mmAl.

The self-adhesive dental/medical composites have a fluoride release of at least 1 µg/cm², preferably at least 1–3 µg/cm², most preferably at least 3–10 µg/cm².

Furthermore the self-adhesive dental/medical composites show a opacity of at least 40%, preferably at least 20–40%, most preferably at least 5–20%.

EXAMPLE 1

Glycerine dimethacrylate-11-bromoundecanoic acid ester

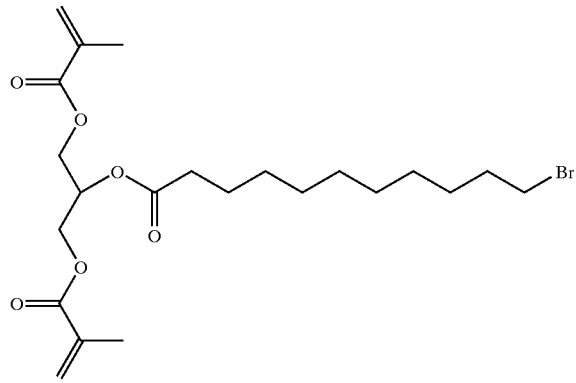

In a 1-1-three necked bottle equipped with a thermometer, condenser and stirrer 75.00 g (0.283 mol) 11-bromoundecanoic acid, 64.55 g (0.283 mol) glycerine dimethacrylate and 1.70 g dimethylamino pyridine were dissolved in 250 ml methylene chloride and cooled to 0–5° C. Under stirring a solution of 64.23 g (0.311 mol) dicyclohexyl carbodiimid were added drop-wise. The resulting suspension was stirred for three hours at 20° C. Then the precipitated solid was removed by filtration and washed three times with 20 ml methylene chloride. The filtrate was cooled to 0° C. over night. The precipitated solid was removed again. Thereafter the solution was washed with 75 ml 1n HCl, 1n NaHCO₃-solution and 2 times with 150 ml water. After drying the organic solution over NaSO₄, 0.1345 g BHT were added and the solvent was removed by vacuum destination (min. 30 mbar, at 40° C.).

Yield: 118.67 g (88.3% of th.)

Glycerine dimethacrylate-11-triethylammonium bromo undecanoic acid ester

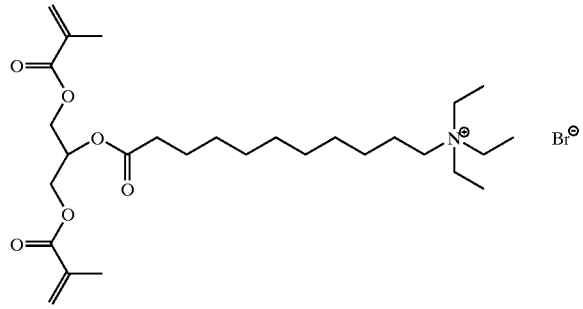

A mixture of 23.77 g (0.050 mol) glycerine dimethacrylate-11-bromoundecanoic acid ester, 6.07 g (0.060 mol) triethylamine in 50 ml ethanol was reflued for 6 hours. Then ethanol and excessive triethylamine was destilled off at 50 to 70° C. and 18 mbar.

Yield: 26.58 g (92.2% of th.)

IR: 2600–2800 cm⁻¹ (absorption of the ammonium salt)

EXAMPLE 2

Glycerine dimethacrylate-11-hydroxy undecanoic acid ester

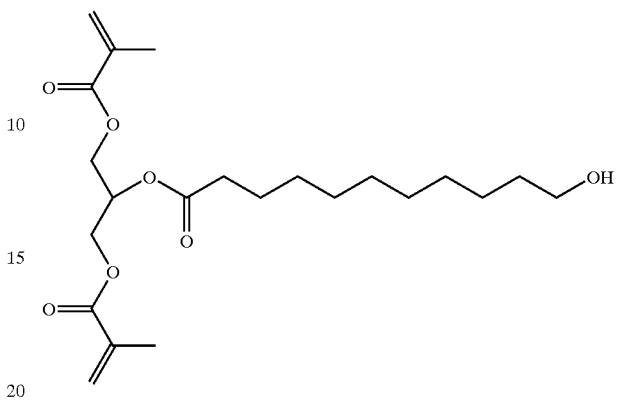

Preparation of Glycerine dimethacrylate-11-bromoundecanoic acid ester according example 1.

To 15.00 g (0.032 mol) glycerine dimethacrylate-11-bromoundecanoic acid ester dissolved in 50 ml ethanol were added 25 ml of sodium hydoxide solution comprising 1.262 g (0.032 mol) NaOH. The mixture was shaked for one hour. Then the crude product was extracted with methylene chloride. The obtained solution was dried over NaSO4 and the solvent was removed.

Yield: 12.50 g (96.0% of th.)

IR: 3430 cm⁻¹ (OH)

Glycerine dimethacrylate-11-(phosphoric acid) undecanoic acid ester

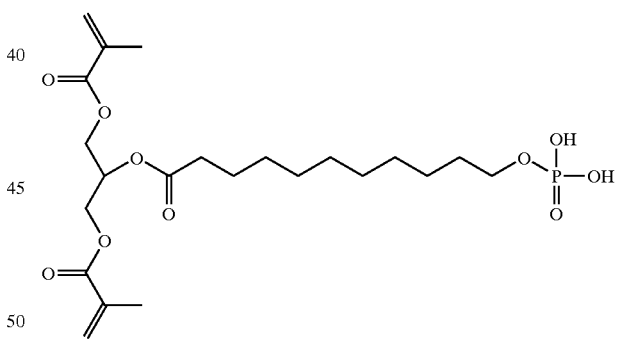

Esterification of the hydroxyl groups of the glycerine dimethacrylate-11-hydroxy undecanoic acid ester with POCl₃.

To 11.551 g (0.028 mmol) of glycerine dimethacrylate-11-hydroxy undecanoic acid ester dissolved in 50 ml THF were added 3.117 g triethylamine in 10 ml THF. After adding 4.723 g POCl₃ (0.031 mmol) drops by drops while stirring at 0° to 5° C. the solution is stirred for further two hours at room temperature. Than the triethylamine hydrochloride is filtered off and the mixture is hydrolysed with 20 ml water. The organic solution is extracted three times with Na₂CO₃ solution and is separated from water. From the solution, dried over MgSO₄, the solvent is evaporated and the macromonomer is dried.

In the IR-spectrum the newly self-adhesive polymerizabe monomer containing phosphoric ester units shows no absorption of hydroxyl groups at □=3400 cm⁻¹. New absorptions were found at □=1007 cm⁻¹, □=2362 cm⁻¹ and as shoulder at □=3302 cm⁻¹. In the ¹H NMR spectrum signals of the olefinic double bonds at $\square_{(CH2=)}$=6.06/6.12 ppm and at $\square_{(CH2=)}$=5.58/5.59 ppm were found. The signals of the methine protons (CH—OP) appears at $\square_{(CH)}$=5.22 and 5.88 ppm. Those of unreacted macromonomer (CH—OH) appears at $\square_{(CH)}$=4.34/4.35 ppm.

Application Example 1 (Dental Adhesive)

1,242 g of the obtained self-adhesive polymerizabe monomer example 2, 0,411 g triethylenglycol dimethacrylate, 0,008 g N,N-bis(□-hydroxyethyl)-p-toluidine and 0,006 g camphor quinone were homogeneously mixed. This mixture was applied in a ring (2 mm high, 5 mm i.d.) on the surface of teeth and exposed with visible light (irradiation lamp Prismetics Lite De Trey Dentsply) for 40 seconds. Immediately after fixation, the teeth were transfered for 24 hours to a chamber at 37±2° C. and 100% relative humidity. The adhesion measured with a Zwick-apparatus is 5.74±1.29 MPa.

Comparative Example 1

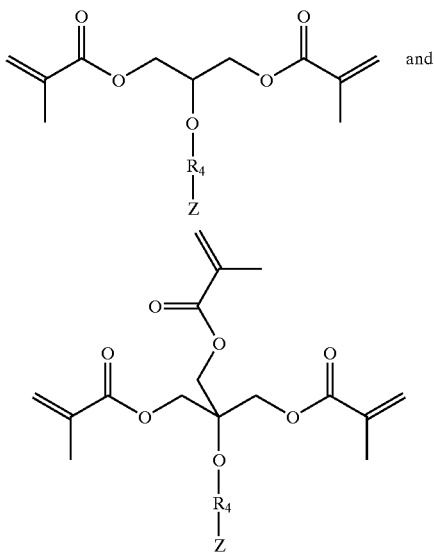

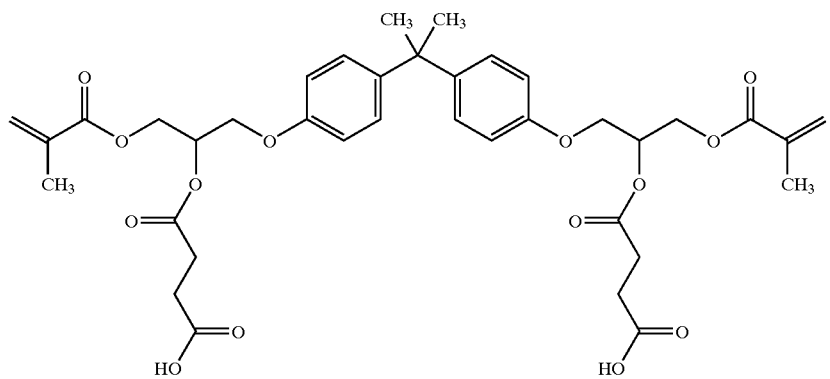

2,420 g of 2,2-Bis-[p-(2-hydroxy-3-methacryloyloxypropoxy)-phenyl]-propan (Bis-GMA) which is modified with succinic anhydride at the hydroxyl groups, 0,821 g tri-ethylenglycol dimethacrylate, 0,016 g N,N-bis(□-hydroxyethyl)-p-toluidine and 0,012 g camphor quinone were homogeneously mixed. This mixture was applied in a ring (2 mm high, 5 mm i.d.) on the surface of teeth and exposed with visible light (irradia-tion lamp Prismetics Lite De Trey Dentsply) for 40 seconds. Immediately after fixa-tion, the teeth were transferred for 24 hours to a chamber at 37±2° C. and 100% relative humidity. The adhesion measured with a Zwick-apparatus is 0.45±0.20 MPa.

We claim:

1. A self-adhesive material comprising a polymerizable monomer having a formula selected from the group consisting of wherein
  $R_4$ denotes a $C_3$ to $C_{20}$ alkylene or a $C_5$ to $C_{20}$ cycloalkylene,
  Z is an acidic moiety selected from the group consisting of

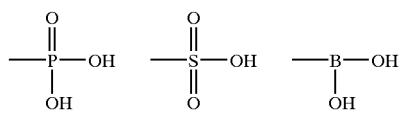

or an ionic moiety selected from the group consisting of

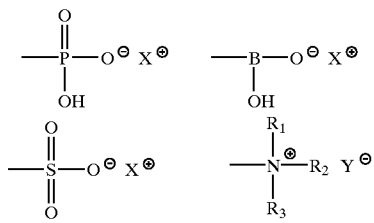

wherein

R$_1$, R$_2$, R$_3$ are the same or different and are hydrogen or residues of a alkylene having 2 to 20 carbon atoms, a cycloalkylene having 5 to 20 carbon atoms, an aryl or a heteroaryl having 4 to 12 carbon atoms, X is a cation selected from the group consisting of ammonium, sulfonium, sodium, potassium, strontium, calcium and magnesium salts, and Y is an anion, selected from the group consisting of OH$^-$, F$^-$, Cl$^-$, Br$^-$, and Tosyl$^-$.

2. A self-adhesive material comprising a polymerizable monomer having the formula

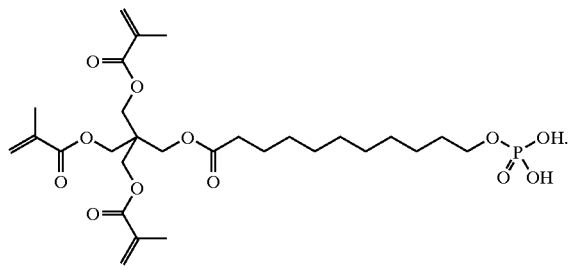

* * * * *